United States Patent [19]
Koeneman

[11] 4,292,695
[45] Oct. 6, 1981

[54] PROSTHESIS STEM

[75] Inventor: James B. Koeneman, Erie, Pa.

[73] Assignee: Lord Corporation, Erie, Pa.

[21] Appl. No.: 162,715

[22] Filed: Jun. 25, 1980

[51] Int. Cl.³ .............................................. A61F 1/24
[52] U.S. Cl. ...................................... 3/1.91; 3/1.912; 128/92 C
[58] Field of Search ................... 3/1.9–1.913; 128/92 C, 92 CA; 433/173, 201

[56] References Cited

U.S. PATENT DOCUMENTS

| | | | |
|---|---|---|---|
| 2,719,522 | 10/1955 | Hudack | 3/1.913 X |
| 3,067,740 | 12/1962 | Haboush | 128/92 CA |
| 3,605,123 | 9/1971 | Hahn | 3/1.9 |
| 3,707,006 | 12/1972 | Bolcros et al. | 3/1.9 |
| 3,855,638 | 12/1974 | Pilliar | 128/92 C X |
| 3,906,550 | 9/1975 | Rostoker et al. | 3/1.912 |
| 3,938,198 | 2/1976 | Kahn et al. | 3/1.192 |
| 3,971,134 | 7/1976 | Bokros | 128/92 C X |
| 4,038,703 | 8/1977 | Bakros | 3/1.91 X |
| 4,164,794 | 8/1979 | Spector et al. | 3/1.91 X |
| 4,231,120 | 11/1980 | Day | 3/1.91 |

FOREIGN PATENT DOCUMENTS

| | | | |
|---|---|---|---|
| 2247721 | 4/1974 | Fed. Rep. of Germany | 3/1.912 |
| 2444831 | 9/1975 | Fed. Rep. of Germany | 3/1.91 |

*Primary Examiner*—Ronald L. Frinks
*Attorney, Agent, or Firm*—Thomas L. Kautz

[57] ABSTRACT

An improved stem portion of a joint prosthesis for replacing a damaged or diseased skeletal joint is provided by the subject invention, wherein a series of sections of elastomeric material attached to a rigid material are disposed one on top of the other in a staggered or offset configuration to form the stem. The offset is such that alternate sections of elastomer and rigid material contact selected locations of the bone within the medullary canal to firmly secure the prosthesis therewithin for resisting dislocation particularly during the early stages of postoperative rehabilitation.

9 Claims, 3 Drawing Figures

PROSTHESIS STEM

FIELD OF THE INVENTION

The present invention relates generally to the field of prostheses, and, more specifically, to an improved stem portion of a joint prosthesis formed to resist dislocation within the medullary canal of the bone adjacent a diseased or damaged human skeletal joint, particularly during the initial bone ingrowth state of postoperative rehabilitation.

BACKGROUND OF THE INVENTION

In recent years, prosthetic devices have been developed and are now in widespread use as attachments, reinforcements or replacements of various members and joints of the human skeletal system. Many modern joint prostheses, including those for replacement of the hip, finger, wrist, elbow and various other joints, are shaped for insertion into the medullary canal of the adjacent bone to secure the prosthesis in place. Synthetic bone cement is one widely used method of securing such prostheses in position within the medullary canal, but it has recently been discovered that problems with this technique include incomplete filling of the cavity of the bone, toxicity of the cement and possible necrosis of the adjacent layer of cancellous or cortical bone. Although bone cement is relatively easy to use in surgical procedures, the above-named problems have prompted development of alternate means of securing prostheses within the medullary canal of the bone adjacent the diseased or damaged joint.

As is well known, bone and tissue ingrowth may be accepted by prostheses formed of materials having a surface porosity of at least 45 microns. Clinical studies have confirmed that bone ingrowth not only avoids the problems of bone cement, but actually provides better stability of the prosthesis over an extended period of time and may result in improved stress distribution between the prosthesis and adjacent bone. Various prior art patents including U.S. Pat. Nos. 3,707,006 to Bokros et al and 3,938,198 to Kahn et al, have recognized the advantage of securing the prosthesis within the medullary canal through bone ingrowth rather than bone cement. As discussed in Bokros et al and Kahn et al, several materials have been utilized to promote bone and tissue ingrowth, including porous ceramic coated with pyrolitic carbon, surface treated titanium, cobalt-chrome and stainless steel alloys and various fibrous overlayers such as polysulfone, Teflon ® coated graphite fiber and polyethylene terephthalate woven mesh.

A major limitation of existing joint prosthesis utilizing bone ingrowth rather than bone cement is that no means are provided to anchor the stem portion of the prosthesis along its entire length within the medullary canal. The Kahn et al patent, for example, discloses a hip joint prosthesis in which the flange portion of the femoral head prosthesis is pinned to the cortical bone of the femur but the stem portion is free to move within the medullary canal of the femur. Recent clinical studies have indicated that movement or shifting of the prosthesis within the medullary canal during the initial four to six weeks of postoperative rehabilitation can interrupt or prohibit bone ingrowth, thus delaying or severely hampering patient recovery. It can be appreciated that the alternative of keeping a patient essentially immobilized for that period of time to avoid such movement of the prosthesis is very difficult.

SUMMARY OF THE INVENTION

The present invention avoids the problems of stability encountered with existing joint prostheses by providing an improved stem portion formed to anchor itself along the entire length of insertion within the medullary canal of the bone adjacent a damaged or diseased joint. The stem portion is formed of a series of alternating sections of elastomer and porous titanium, or a suitable equivalent, which are disposed one on top of the other in a staggered or offset configuration. This offset configuration results in alternate sections of elastomer-titanium contacting various locations on the walls of the medullary canal as discussed below. The elastomer-titanium sections are dimensioned such that the stem portion of the prosthesis is of a diameter larger than that of the medullary canal. The layers of elastomer are stressed in shear as the stem is inserted into position, and urge the adjacent sections of titanium into contact with the medullary canal to securely hold the prosthesis therewithin.

It is therefore an object of the present invention to provide an improved stem portion of a joint prosthesis for insertion into the medullary canal of the bone adjacent a diseased or damaged human skeletal joint.

It is another object of the subject invention to form the stem portion of a prosthesis of a plurality of alternating sections of elastomer and porous titanium which are disposed one on top of the other in a staggered or offset configuration, such that upon insertion of the stem portion into the medullary canal the elastomer layers are stressed in shear to urge the adjacent titanium sections outwardly into contact with the walls of the medullary canal for securely holding the prosthesis in place as initial bone ingrowth takes place.

DESCRIPTION OF THE DRAWINGS

Objects in addition to the foregoing will become apparent upon consideration of the following description taken in conjunction with the drawings wherein.

DETAILED DESCRIPTION OF THE INVENTION

Figure 1:
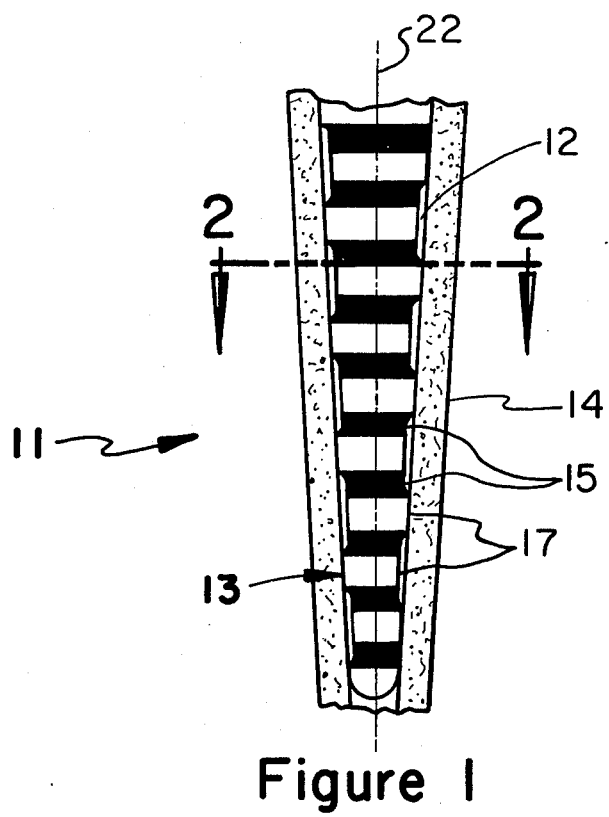
FIG. 1 is a partial front view of the stem portion of the present invention.

Referring now to the drawings, the stem portion of the present invention is labelled generally with the reference 11. Stem portion 11 may be formed in the shape of the medullary canal 12 of the femur, tibia, metacarpals, humerus, ulna and various other bones (labelled generally as 14) in the human body depending on the damaged or diseased joint to be replaced by the prosthesis. In this embodiment, stem portion 11 consists of a plurality of individual sections 13 of a resilient, generally circular layer of elastomeric material 15 bonded to a correspondingly shaped rigid layer 17 formed of titanium, cobalt-chrome, stainless steel or a biocompatible polymeric material. The elastomeric material 15 may be bonded to rigid layer 17 by vulcanization, adhesive coatings or any other suitable means. The rigid layers 17 are preferably treated in a known manner to produce a surface porosity of at least 45 microns, which is capable of accepting bone and tissue ingrowth.

Figures 2, 3:
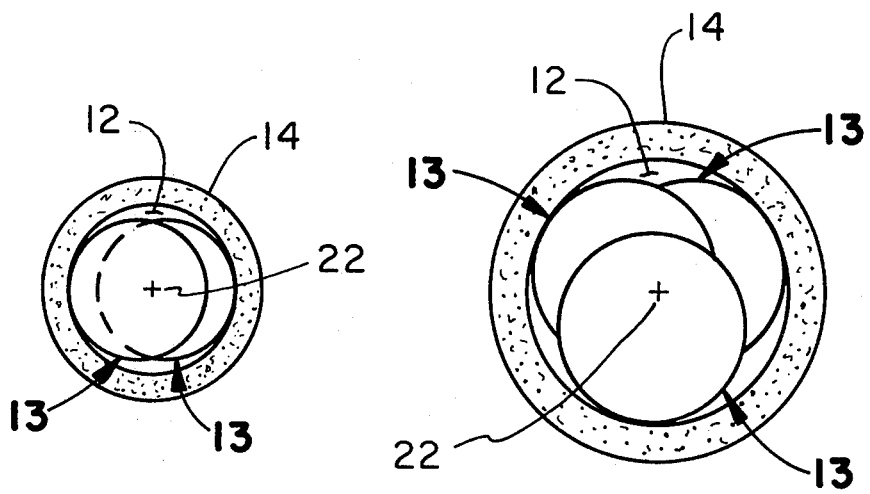
FIG. 2 is a partial cross-sectional view taken generally along the line 2—2 of FIG. 1.
FIG. 3 is a partial cross-sectional view of an alternate embodiment of the subject invention.

Stem portion 11 is formed by bonding a series of sections 13, one on top of the other, in an offset or staggered configuration. As shown in FIG. 1, the elastomeric material 15 of one section 13 is bonded to the bottom surface of the rigid layer 17 of an adjacent section 13. In forming the complete stem 11 of a prosthesis, each succeeding section 13 is offset from the section 13 immediately above and below (except for the end sections). As illustrated in the cross-sectional views of stem 11 shown in FIGS. 2 and 3, taken perpendicular to the longitudinal axis 22 of stem 11, it is contemplated herein that the offset may be varied depending upon how many different points of contact between the sections 13 and the bone 14 are needed to obtain the desired stability of stem 11. In the embodiment of FIG. 2 for example, adjacent sections 13 are laterally offset from one another along axes disposed on opposite sides of the longitudinal axis 22 of stem 11, which are parallel to and equidistant from longitudinal axis 22. This offset results in two points of contact between the sections 13 and the bone 14 such that the outer edge of alternate ones of the sections 13 contact one location on the bone 14, and the outer edge of the other sections 13 contact a second location on the bone 14 approximately 180° from the first location.

An alternative embodiment is shown in FIG. 3 in which adjacent sections 13 are laterally offset from one another such that the point of contact between each section 13 and bone 14 within the medullary canal 12 is offset 120° from the adjacent section 13 above and below (except, of course, for the bottom and top sections). In this instance, every third section 13 along the length of stem 13 is disposed along a common axis, thus forming three separate axes within stem 11 in addition to the longitudinal axis 22. The three common axes of stem sections 13 are parallel to the longitudinal axis 22 and spaced at 120° intervals from one another at an equal radial distance from longitudinal axis 22. As mentioned above, various other offsets may be utilized to obtain proper stability of stem 11 and those shown in FIGS. 2 and 3 are merely illustrative of the concept herein.

The diameter of stem portion 11, which is the diameter of the smallest circle which contacts the outer edge of two adjacent sections 13 in the embodiment of FIG. 2 of three adjacent sections 13 in the embodiment of FIG. 3, is sized to be greater than the diameter of the medullary canal 12 into which the stem 11 is inserted. When inserted into the medullary canal 12, the elastomeric material 15 deflects and is stressed in shear by the rigid layers 17 immediately above and below. As a result, each rigid layer 17 is urged outwardly into contact with the adjacent walls of the medullary canal 12 and resists dislocation of the prosthesis which could result from movement of the patient during the initial stages of bone ingrowth.

The improved stem portion of the present invention is thus formed to be held along its entire length within the medullary canal, unlike prior art prosthesis which have no means to directly secure the stem and are typically pinned or held by bone screws at a single location. The stability provided by the present invention to a joint prosthesis greatly reduces the chances of obtaining inadequate or improper bone and tissue ingrowth during the initial stages of postoperative rehabilitation and thus enhances and accelerates patient recovery.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. In a joint prosthesis for replacing a skeletal joint in the human body, the improvement comprising a prosthesis stem having a longitudinal axis and being shaped for insertion into the medullary canal of the bone adjacent said skeletal joint, said stem including a plurality of individual sections formed of a layer of resilient elastomeric material attaching to a layer of rigid material, said individual sections being attached one on top of the other in an offset configuration to form said stem, the outer edges of at least two adjacent ones of said individual sections defining the diameter of said stem, said diameter of said stem being greater than the diameter of said medullary canal whereby upon insertion of said stem into said medullary canal said layers of elastomeric material deflect in shear and urge said layers of rigid material into contact with said bone for resisting dislocation of said stem within the medullary canal.

2. The prosthesis stem of claim 1 wherein said layers of rigid material are formed from material selected from the group consisting of titanium, cobalt-chrome, stainless steel alloys, or a biocompatible polymeric material.

3. The prosthesis stem of claim 2 where said layers of rigid material are treated to obtain a surface porosity of at least 45 microns.

4. The prosthesis stem of claim 1 wherein essentially one-half of said individual sections are laterally offset from the other half of said individual sections, each half of said individual sections being in alignment and being disposed along an axis parallel to and radially offset from the longitudinal axis of said stem.

5. The prosthesis stem of claim 1 wherein said individual sections are attached one on top of the other in a 120° offset configuration, the center of each of said individual sections being offset 120° from the centers of the immediately adjacent individual sections, every third one of said individual sections being in alignment and being disposed along an axis parallel to and radially offset from the longitudinal axis of said stem.

6. In a joint prosthesis for replacing a skeletal joint in the human body, the improvement comprising a prosthesis stem having a longitudinal axis and being shaped for insertion into the medullary canal of the bone adjacent said skeletal joint, said stem including a plurality of individual sections formed of a layer of resilient elastomeric material attaching to a layer of rigid material, said individual sections being attached one on top of the other to form said stem, alternate ones of said individual sections being offset from the other sections and disposed along a first axis parallel to and radially spaced from the longitudinal axis of said stem, said other individual sections being disposed along a second axis parallel to and radially spaced from the longitudinal axis of said stem, said first axis being offset 180° from said second axis relative to said longitudinal axis, the outer edges of two adjacent individual sections defining the diameter of said stem, said diameter of said stem being greater than the diameter of said medullary canal whereby upon insertion of said stem into said medullary canal said layers of elastomeric material deflect in shear and urge said layers of rigid material into contact with the bone for resisting dislocation of said stem within the medullary canal.

7. The prosthesis stem of claim 6 wherein said layers of rigid material are formed from material selected from the group consisting of titanium, cobalt-chrome, stainless steel alloys or a biocompatible polymeric material.

8. The prosthesis stem of claim 7 wherein said layers of rigid material are treated to obtain a surface porosity of at least 45 microns.

9. In a joint prosthesis for replacing a skeletal joint in the human body, the improvement comprising a prosthesis stem having a longitudinal axis and being shaped for insertion into the medullary canal of the bone adjacent said skeletal joint, said stem including a plurality of individual sections formed of a layer of resilient elastomeric material attaching to a layer of rigid material, said individual sections being attached one on top of the other in a 120° offset configuration to form said stem, the center of each individual section being offset 120° from the centers of the immediately adjacent individual sections, the centers of every third one of said individual sections being disposed along a common axis parallel to and radially offset from the longitudinal axis of said stem such that the outer edges of three adjacent individual sections define the diameter of said stem, said diameter of said stem being greater than the diameter of said medullary canal whereby upon insertion of said stem into said medullary canal said layers of elastomeric material deflect in shear and urge said layers of rigid material into contact with the bone for resisting dislocation of said stem within the medullary canal.

* * * * *